United States Patent [19]

Watanabe

[11] 4,035,304
[45] July 12, 1977

[54] BLOOD FILTERING BAG

[75] Inventor: Masaharu Watanabe, Ichikawa, Japan

[73] Assignee: Terumo Corporation, Tokyo, Japan

[21] Appl. No.: 590,080

[22] Filed: June 25, 1975

[30] Foreign Application Priority Data

July 5, 1974 Japan .................. 49-79667[U]

[51] Int. Cl.² .................................. A61M 5/46
[52] U.S. Cl. ........................... 210/317; 128/214.2; 210/445; 210/446; 210/495; 210/500 R; 210/DIG. 23
[58] Field of Search ....... 128/214 C, 214 D, 214 R, 128/214.2; 210/317, 335, 336, 337, 338, 339, 445, 446, 451, 453, 483, 485, 489, 495, 499, 500 R, 503, DIG. 23

[56] References Cited

U.S. PATENT DOCUMENTS

| | | | |
|---|---|---|---|
| 2,644,586 | 7/1953 | Cutter | 210/448 X |
| 2,765,923 | 10/1956 | Novak | 210/DIG. 23 |
| 3,217,889 | 11/1965 | Berg | 210/499 X |
| 3,419,151 | 12/1968 | Smith et al. | 210/489 X |
| 3,506,130 | 4/1970 | Shaye | 210/DIG. 23 |
| 3,557,786 | 1/1971 | Barr et al. | 128/214 C |
| 3,675,780 | 7/1972 | Marshall et al. | 210/495 X |

FOREIGN PATENT DOCUMENTS

| | | | |
|---|---|---|---|
| 667,933 | 11/1952 | United Kingdom | 128/214 C |
| 717,733 | 11/1954 | United Kingdom | 128/214 C |

*Primary Examiner* — Thomas G. Wyse
*Assistant Examiner* — R. G. Mukai
*Attorney, Agent, or Firm* — Carroll F. Palmer

[57] ABSTRACT

Disclosed is a blood filtering bag comprising a bag body provided with a blood inlet and a blood outlet, and a filter supported by a support member and dividing the bag body into two parts — inlet side part and outlet side part. The support member is thermally fused to a peripheral portion of the bag body.

2 Claims, 8 Drawing Figures

4,035,304

BLOOD FILTERING BAG

FIELD OF THE INVENTION

This invention relates to a blood filtering instrument for filtering the blood to remove denatured blood components or other harmful components to a human body, and more particularly to a bag-type filtering instrument in which a filter comprising a plurality of sheet-like filtering members is incorporated.

Brief Description of the Prior Art

Generally, there is an increasing tendency that the reserve blood of a blood bank is used as transfusion blood. It is known, however, that where the blood is kept in an appropriate reserve condition after or, denatured blood components such as lumps of viscous platelets, agglutinations of wire corpuscles start to be created in about several hours after blood collection. In the case where an external circulation of blood is performed during a surgical operation, an artificial dialysis, or the like, such denatured blood components are not only formed but also there is a possibility that alien substances such as pieces of epithelium, small pieces of muscle, lipid or air may enter into the body of a blood recipient. When such denatured blood components and alien substances are introduced into the body of a blood recipient, an adverse action such as incompletion of blood circulation, or a disease is caused, or induced. For this reason, a blood transfusion device has incorporated therein a blood filtering instrument for removing the denatured components of the blood or the alien substances in the blood.

As such blood filtering instrument there is known the one which is constructed such that, for example, a polyester fibre is packed with high density in a hard plastic-made housing. This kind of blood filtering instrument, however, indeed provides a high filtering efficiency but has the drawback that it is difficult to manufacture uniform products as a result of requiring packing such fibre with as considerably high a density as 0.1 to 0.4 g/cm$^3$; and channeling (that is, the phenomenon that the blood selectively passes through the fibre portions of lower density) takes place. In order to prevent the occurrence of such channeling, the fibre has to be charged in the housing with an appreciable great thickness, so that in the case of, for example, mass transfusion pores in the filter are likely to be closed. In order to avoid this pore-closing the filtering area has to be enlarged with the result that upon blood filtering the priming volume and residual volume of blood are increased; and in quick transfusion the filtering resistance is greatly increased.

U.S. Pat. No. 3,765,537 (Rosenberg) discloses a blood filtering instrument wherein a filter element consisting of a first filter sheet comprising open netting of plastic filament having a pore size of about 800 to about 4000 microns and a second filter sheet comprising open mesh fabric of a plastic monofilament having a pore size of about 20 to about 50 microns is incorporated in a housing or bag in a corrugated form. This blood filtering instrument has a wide filtering area and therefore raises no problem as far as the mass transfusion and quick transfusion are concerned, but is not very excellent in respect of the filtering efficiency.

As above described, in the prior art filtering instrument, filtering efficiency and the filtering resistance run counter to each other and the user is compelled to select either of both properties.

SUMMARY OF THE INVENTION

An object of the invention is to provide a blood filtering instrument which has low filtering resistance and high filtering efficiency.

Another object of the invention is to provide a flexible bag-type blood filtering instrument which is easy to manufacture and is capable of being miniaturized.

According to the invention, there is provided a blood filtering bag comprising a flat bag body formed of flexible, thermally fusible synthetic resin, blood inlet and outlet provided on said bag body, and a flexible sheet-like filter dividing the interior of said bag body into two parts one of which is an inlet side part and the other of which is an outlet side part, wherein said filter is supported by a support member thermally fused to a peripheral portion of said filter, the peripheral portion of said support member being thermally fused to an edge portion of said body.

DETAILED DESCRIPTION OF THE INVENTION

Figure 1:
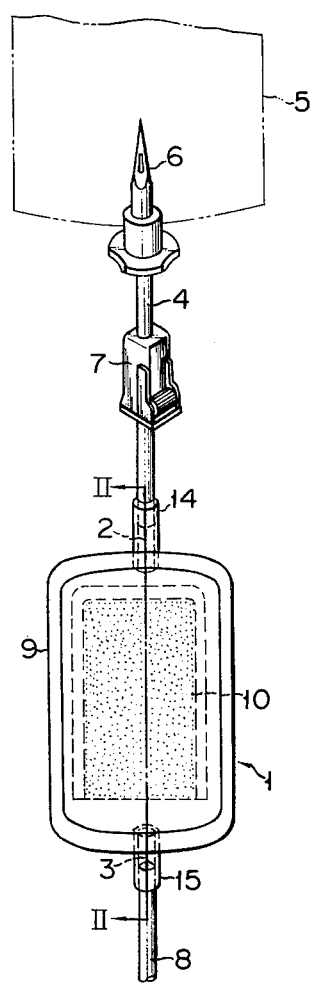
FIG. 1 is a plan view of a blood filtering bag according to the invention.

This invention is hereinafter described in detail by reference to the appended drawings. Throughout the drawings the same parts and sections are denoted by the same reference numerals.

In FIG. 1, a blood filtering bag 1 of the invention is incorporated in a blood transfusion device. The blood filtering bag 1 has a body 9, which has a blood inlet 2 and a blood outlet 3 at its both ends. The blood inlet and outlet 2, 3 are formed in pipes 14, 15 attached to said both ends of the bag body 9 of the bag 1. To the pipe 14 is connected a flexible tube 4 having at its tip end a bottle needle 6 piercing into the bottom section of a blood receptacle 5. A clamp 7 is mounted or fitted over the flexible tube 4 at a halfway portion thereof, and by properly depressing the flexible tube 4 by means of this clamp 7 the flow quantity of blood flowing through the flexible tube 4 is controlled. Further, to the pipe 15 provided on the bag 1 is connected a flexible tube 8, which is connected to a blood transfusion device body (not shown).

Figure 2:
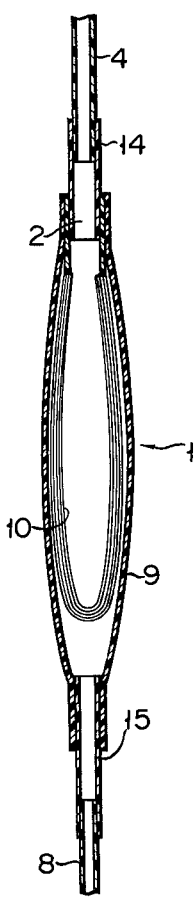
FIG. 2 is a sectional view taken along the line II—II of FIG. 1.

The blood filtering bag 1 has a bag body 9, which is formed of soft and thermally fusible synthetic resin such as polyvinyl chloride. As best shown in FIG. 2, the interior of the bag body 9 is divided, by a flexible filter 10 bent into a U-shape into two parts — inlet side part and outlet side part. The blood introduced from the inlet 2 has its harmful component removed while being passed through the filter 10, and the purified blood is discharged from the outlet 3. The U-shaped filter 10, as later described, has its side portions sealed to a support member 13 by thermal fusion and is secured to the bag body 9 through this support member.

Figure 3:
FIG. 3 is a detailed cross sectional view of a part of the filter used in the blood filtering bag according to the invention.

As shown in FIG. 3, the filter 10 consists of plural, for example, five sheet-like filter elements 11a, 11b, 11c, 11d and 11e superposed one upon another in the order mentioned, that is, in the order in which blood is passed. The element 11a consists of open mesh netting of a plastic filament having a pore size of 100 to 250 microns and functions to remove relatively coarse harmful components. The elements 11b, 11c, 11d and 11e function to remove relatively fine harmful components and each consist of nonwoven synthetic fabric having a pore size of 10 to 80 microns. This fabric is preferably of a "no-binder" type made of endless yarns of a thermally fusible resin such as nylon, polyester or the like, for example, those formed of 6-nylon endless yarn having a density of 0.21 g/cm$^3$, a pore volume of 1.53 cm$^3$/g, a porosity of 46% and an average pore size of 20 to 30$\mu$, and having a density of 0.30 g/cm$^3$, a pore volume of 1.41 cm$^3$/g, a porosity of 30% and an average pore size of 15 to 30$\mu$ are preferably used as said fabric. These no-binder type non-woven fabrics are chemically and physically safe and yet produce few flocks.

As above described, by using the sheet-like filter elements consisting of nonwoven fabrics, the filtering resistance is made small to permit a rapid transfusion, and further the filtering area is enlarged to increase the filtering efficiency and simultaneously to permit a large amount of blood to be treated at one time. Channeling can also be prevented by properly superposing a plurality of said elements one upon another. Note that the above-mentioned filter elements 11b, 11c, 11d and 11e may each consist of a plastic filament-made open mesh netting or porous fiber sheet having a pore size of 20 to 80 microns.

Figure 4A:
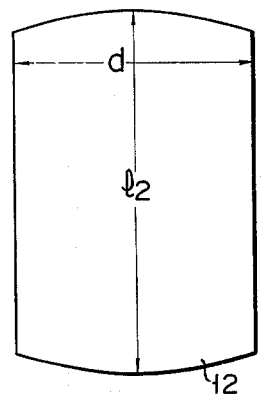
FIGS. 4a–4c present a dismembered view of the blood filtering bag of the invention shown in FIG. 1.
Figure 4B:
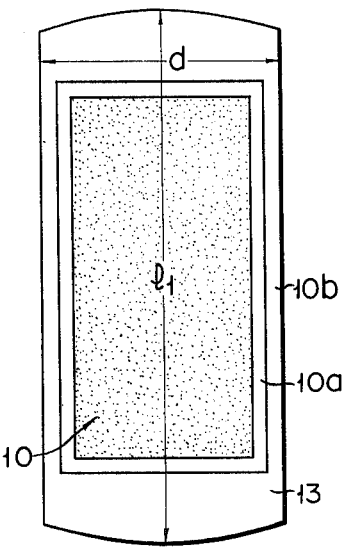
Figure 4C:
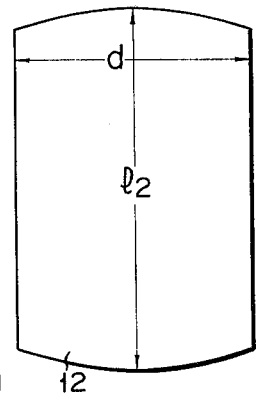

As shown in FIG. 4, the bag body 9 is constituted by, for example, a pair of polyvinyl chloride sheets 12, 12. The blood filter 10 having the above-mentioned construction is supported by the sheet-like support member 13 having a thermal fusibility to the synthetic resin forming the bag body 9. Material constituting the support member 13 is the same quality of material as that constituting the sheets 12, 12, that is to say, polyvinyl chloride. But this material may be a different quality of material from that of the sheets 12, 12, that is to say, a thermally fusible material. Selection of such material quality will be obvious to those skilled in the art. This support member 13 is a frame-like sheet whose central part is bored, and the filter 10 is situated at the bored part of the support member 13 and the entire peripheral edge portion 10a of the filter 10 is thermally fused to the peripheral edge portion of the support member 13. The support member 13, even after the thermally fused portion 10a is excluded, still remains to have a portion 10b which is thermally fusible to the sheets 12, 12. The width $d$ of the support member 13 is the same as the width of the sheets 12, 12, and the length $l_1$ thereof is larger than the length $l_2$ of the sheets 12, 12 while the half of the length $l_1(l_1/2)$ is smaller than the latter $l_2$.

Figure 5:
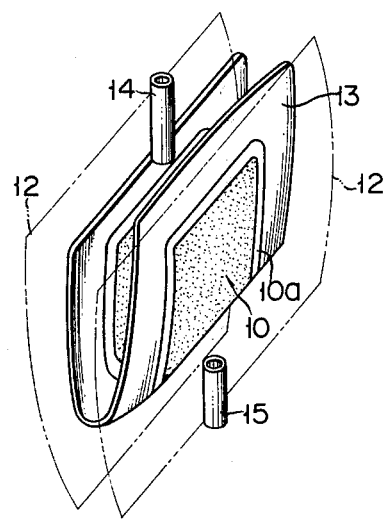
FIG. 5 is a view for explaining the procedure of manufacturing the blood filtering bag of the invention shown in FIG. 1.

In order to manufacture the blood filtering bag according to the invention having the foregoing construction, as shown in FIG. 5, the pair of sheets 12, 12 constituting the bag body 9 are disposed opposite to each other, and the filter 10 previously attached to the support member 13 is longitudinally folded in two and is disposed between the sheets 12, 12. Further, the pipe 14 constituting the inlet 2 is inserted between both opposed end portions of the support member 13, while the pipe 15 constituting the outlet 3 is inserted between the lower end edge portions of the sheets 12, 12, and the pipes 14, 15 are coaxially so arranged as to oppose each other. When, under this condition, bonding is carried out while the respective entire peripheral edge positions of the sheets 12, 12 and the support member 13 are being heated in a state wherein said entire peripheral edge portion of the support member 13 is interposed between said sheets 12, 12. Accordingly, the filter 10, as shown in FIG. 2, is disposed baggily within the bag body 9 in a state bent into a U-shape, and divides the bag body interior into two parts — the inlet side part and outlet side part.

The filter 10, as previously mentioned, is formed of nylon, polyester, or the like, and such material has a higher fusing point than the polyvinyl chloride of which the support member is formed, so that when such material is thermally fused to the support member 13, there are likely to be created the parts where fusion is incomplete, that is to say, what is called pinholes. Since, however, upon manufacture of the blood filtering bag 1 of the invention, the step of beforehand attaching the filter 10 to the support member 13 can be executed as previously mentioned, creation of such pinholes can be avoided as much as possible. In addition, even if such pinholes are created, it will cause no damage to a finished filtering bag, which offers a great economical advantage. Further, detection of said parts where fusion is incomplete can be performed under the condition wherein the filter 10 is attached to the support member 13, which offers a great convenience. Further, where the blood filtering bag 1 is assembled as a whole, the support member 13 having the filter 10 has only to be thermally fused to the sheets 12, 12, which simplifies the assembling operation. Further, the material for constituting the support member 13 can be the same as, or the one having thermal fusibility to, that for constituting the bag body 9, which does not cause the pinholes to be created.

There will now be described the filtering operation of the blood filtering bag 1 having the said construction. The bottle needle 6 of the blood transfusion device is pierced into the bottom of the blood receptacle 5, thereby connecting the blood transfusion device to the blood receptacle 5. Subsequently, the clamp 7 is loosened to cause the blood in the receptable 5 to flow down from the inlet 2 into the blood filtering bag 1 through the flexible tube 8. In the blood filtering bag 1, the blood having flowed thereinto from the inlet is collected in the sheet-like filter 10 which is bent into a U-shape to assume a baggy configuration as shown in FIG. 2. Thereafter, said blood is passed through the elements 11a, 11b, 11c, 11d and 11e in the order mentioned, and during this passage the denatured components or alien substances contained in the blood are caught by said elements 11a, 11b, 11c, 11d and 11e. The respective elements 11a, 11b, 11c, 11d and 11e have flexibility, and as the blood passes through them, the filter 10 constituted by them is forcibly expanded by the blood to cause the filter elements to be separated from each other. As a result, the effective filtering area of each filter element is increased. The bag body 9 also has flexibility, and therefore, as the filter elements are forcibly expanded, the bag body 9 is similarly expanded and therefore does not interrupt the above-mentioned filtering action. The purified blood passed through the filter 10 is once gathered at the bottom section of the bag body 9, and thereafter the blood thus gathered flows from the outlet 3 into a dripping cylinder (not shown) and then into an injection needle (not shown) of the blood transfusion device, through the flexible tube 8.

As above described, the blood filtering bag of the invention consists of a combined unit of the flexible sheet-like filter and the flat flexible bag body and therefore can be made flat and yet miniaturized as a whole. Further, this bag can be properly expanded in accordance with the quantity of blood flowing thereinto, so that the whole surfaces of the respective filter elements effectively participate in the blood filtering without the production of any dead space in the bag interior. Further, even where, in performing the intermittent transfusion, the blood separation takes place within the bag, the separated blood can be readily remixed by manually crumpling the bag. Further, the filtering area is extremely large as compared with the respective areas of the inlet and outlet, and therefore a decrease in the filtering efficiency due to the variation in the flow speed of the blood little is mitigated.

Figure 6:
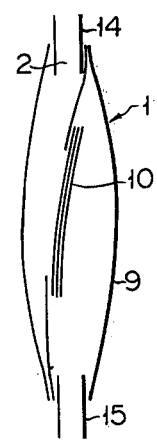
FIG. 6 is a schematic sectional view of another filtering bag according to the invention.

In the preceding embodiment, the filter 10 is disposed within the bag body 9 in a state bent into a U-shape. But this invention is not limited to this type of disposition, and for example, as shown in FIG. 6, the support member may be fused to those respective portions of the inlet 14 and outlet 15 which are diagonally opposite to each other, in a state wherein the filter 10 remains flat or linear, thereby dividing the interior of the bag body into two parts. Further, the filter of the invention may be the one prepared by modifying the bottom of the U-shaped filter shown in FIG. 1 or 2 into a W-configuration, and further may be the one prepared by two folding an intermediate portion of the flat filter shown in FIG. 6 into an S-configuration. In any case, the blood filtering bag of the invention is rendered flat as a whole, and this flat construction is for the first time obtained by providing the support member 13.

What is claimed is:

1. A blood filtering bag comprising:
a flat bag formed of two sheets of flexible polyvinyl chloride resin, peripheral portions of the sheets being thermally fused together, forming a blood passageway between the sheets;
blood inlet and outlet provided on the bag body;
a support member of polyvinyl chloride resin thermally fused between the peripheral portions of said two sheets and having a substantial free area extending from said fused portions into the blood passageway; and
a flexible sheet-like filter formed of nylon filaments diagonally arranged in the blood passageway partitioning the same into a blood inlet side part and a blood outlet side part, the peripheral portion of the filter being thermally fused to the free area of said support member so that the filter is supported and sealed by said support member.

2. A blood filtering bag comprising:
a flat bag body formed of a pair of rectangular sheets of flexible, polyvinyl chloride resin comprising opposed short sides and opposed long sides, peripheral portions of the sheets being thermally fused together, forming a blood passageway between the sheets;
blood inlet and outlet respectively provided on the opposed short sides of the bag body;
a support member comprising a rectangular frame of polyvinyl chloride resin; and
a flexible rectangular sheet-like filter covering a rectangular central opening in said frame, the perifery of said filter overlapping said frame and fused to the same, leaving a substantial free peripheral area to the frame comprising two opposed short side portions and two opposed long side portions, said filter comprising a plurality of superposed filter elements each formed of a binderless nonwoven fabric sheet formed of fibers of nylon or polyester and having a pore size of 20 to 80 microns and an open mesh netting made of nylon or polyester filaments and having a pore size of 100 to 250 microns, wherein the free area of said opposed short side portions of said frame are thermally fused together between the blood inlet side portions and said opposed long side portions of the frame are thermally fused together between opposed long side portions of said sheets.

* * * * *

UNITED STATES PATENT OFFICE
CERTIFICATE OF CORRECTION

PATENT NO. : 4,035,304
DATED : July 12, 1977
INVENTOR(S) : Masaharu Watanabe

It is certified that error appears in the above-identified patent and that said Letters Patent are hereby corrected as shown below:

Column 6, line 36, "and having a pore size of 20 to 80 microns" should be deleted; and Column 6, lines 38 to 39, "and having a pore size of 100 to 250 microns" should be deleted.

Signed and Sealed this

Twenty-fifth Day of October 1977

[SEAL]

Attest:

RUTH C. MASON
Attesting Officer

LUTRELLE F. PARKER
Acting Commissioner of Patents and Trademarks